United States Patent [19]

Grolman

[11] Patent Number: 5,671,039
[45] Date of Patent: Sep. 23, 1997

[54] GLARE TESTER

[75] Inventor: Bernard Grolman, Worcester, Mass.

[73] Assignee: Leica Inc., Depew, N.Y.

[21] Appl. No.: 962,859

[22] Filed: Oct. 19, 1992

[51] Int. Cl.⁶ .................. A61B 3/02; A61B 3/10
[52] U.S. Cl. .................. 351/243; 351/213; 351/214; 351/217
[58] Field of Search .................. 351/205, 206, 351/211, 217, 243, 235, 221, 222, 246–247; 359/601, 608–610, 614, 227, 229, 234–236

[56] References Cited

U.S. PATENT DOCUMENTS

| | | | |
|---|---|---|---|
| 1,806,318 | 5/1931 | Tillyer | 351/217 |
| 3,498,699 | 3/1970 | Wilkinson | 351/235 |
| 4,550,990 | 11/1985 | Trispel et al. | 351/222 |
| 4,764,007 | 8/1988 | Task | 351/222 |
| 4,800,404 | 1/1989 | Ginsburg et al. | 351/243 |
| 5,281,984 | 1/1994 | Burlow et al. | 351/221 |

FOREIGN PATENT DOCUMENTS

| | | | |
|---|---|---|---|
| 3037466 | 5/1981 | Germany | 351/217 |
| 458730 | 12/1936 | United Kingdom | 351/217 |

*Primary Examiner*—Thong Nguyen
*Attorney, Agent, or Firm*—Bean, Kauffman & Snyder

[57] ABSTRACT

A glare tester suitable for use with conventional subjective refractors for testing visual acuity is disclosed. The tester may be fitted to new refractors or retrofitted to existing refractors. The preferred tester is a plastic annular ring with a plurality of LEDs mounted in recesses to direct light toward the test axis and a surface to reflect the LED light toward the patient's eye. A coating on the ring surface opposite the patient's eye improves the LED efficiency.

20 Claims, 3 Drawing Sheets

GLARE TESTER

BACKGROUND OF THE INVENTION

The present invention relates to devices for testing the acuity of the eye and, more particularly, for comparing the acuity of an eye with and without induced glare.

Devices for acuity glare testing usually direct bright light from a source at an eye under test while the patient attempts to identify symbols on a chart. Most devices of this type are separate and apart from the refractor used for normal acuity testing. U.S. Pat. No. 4,859,051 issued Aug. 22, 1989 is an exception that discloses an objective/subjective refractor having a glare testing feature. The feature is used during subjective testing with light from sources 33 at a position adjacent to the acuity chart 32b. U.S. Pat. Nos. 3,684,355 and 4,800,404 issued Aug. 15, 1972 and Jan. 24, 1989, respectively, disclose glare testing devices that direct light toward a patient's eye, or eyes, while the patient attempts to read a target. These latter patents do not teach or disclose refraction correcting lenses as part of the device. Such devices have the disadvantage that they require separate space when not in use and are more susceptible to damage or breakage.

Many prior art devices are intended to determine a patient's night acuity. Such devices use a darkened room and are not useful for determining functional acuity under daytime conditions and usually do not provide quantitative information that permits systematically tracking changes in the eye. For example, the glare tester of the present invention permits quantitative tracking of cataract development. An eye with lenticular opacities of diverse densities will scatter incoming light in relation to the density and location of the opacities. The consequence of the scattered light appears to the patient as a veiling glare over the principal retina that diminishes the patients acuity. A glare tester according to the present invention permits the clinician to objectively track development of a cataract and systematically decide when removal of the cataract is appropriate.

One object of the present invention is to eliminate the disadvantage of a separate unit for conducting glare testing during refraction examination.

Another object of the present invention is to provide a means of conducting glare testing without modification of the symbol projection system or acuity charts.

Another object of the present invention is the introduction of glare testing means into an existing refraction instrument.

A conventional refractor has a plurality of disks with each of several disks supporting a number of lenses, each of which has a different power. By rotating one or more of the disks, the practitioner can place on the test axis the appropriate lenses to correct for normal refractive errors of a patient's eye. Most conventional refractors also have one auxiliary disk adapted to support a number of special accessories that can be selectively placed on the test axis in addition to any lens that have been selected. One conventional refractor of this type with an auxiliary disk is disclosed in U.S. Pat. No. 3,498,699 issued Mar. 3, 1970.

SUMMARY OF THE INVENTION AND DRAWINGS

This invention is directed to a subjective refractor containing means for glare testing and, more particularly, a conventional refraction device used in conjunction with a projected test symbol or a wall chart and that incorporates means for selectively subjecting the eye or eyes being refracted to glare. A source of glare illumination is mounted on the auxiliary disk at an empty aperture. Preferably, the source includes a plurality of discrete sources, such as LEDs, supported by a plastic disk that direct scattered light toward the eye. The side of the ring opposite the eye can be coated with a reflective material to increase the efficiency and the glare illumination can be turned on, off, the intensity infinitely varied or momentarily flashed by a control.

DESCRIPTION OF THE PREFERRED EMBODIMENT

Figure 1:
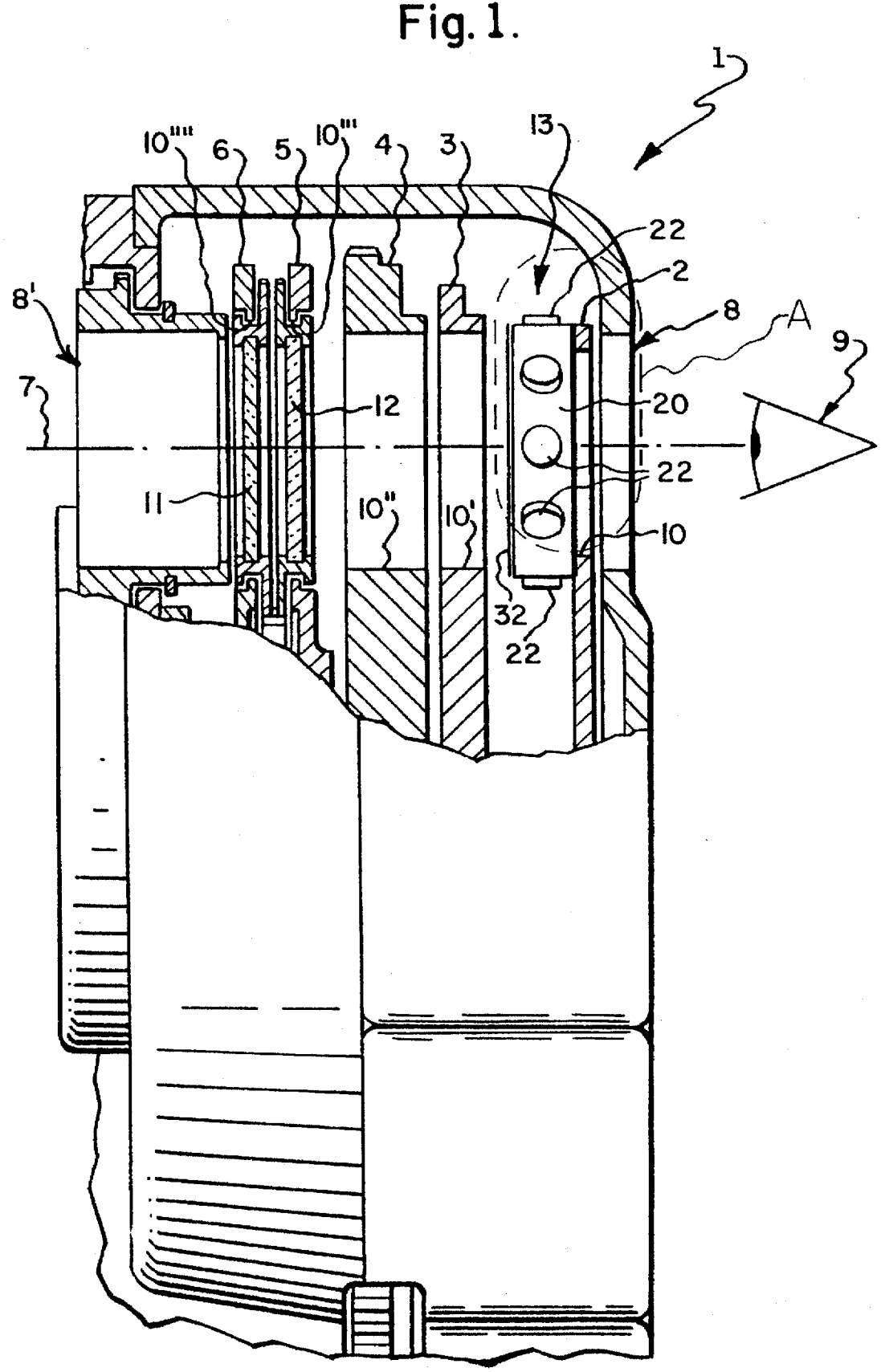
FIG. 1 is a schematic cross-section of a portion of one battery of a refractor according to the present invention.

Referring to FIG. 1, refractor battery 1 has body 1a, auxiliary disk 2, strong sphere disk 3, weak sphere disk 4, strong cylinder disk 5 and weak cylinder disk 6. Each of disks 2–6 have a multiplicity of apertures 10, 10', 10", 10''' and 10'''' (only one shown in each disk) that contain an accessory, lens or an opening adapted to receive an accessory or lens. Test axis 7 passes through the center of windows 8, 8' of refractor 1, as well as a selected aperture in each of disks 2–6, and is aligned with eye 9. By selectively rotating disks 3–6, an open aperture or selected lens may be presented by each disk on test axis 7, such as weak cylinder lens 11 and strong cylinder lens 12. Glare tester 13 is attached to auxiliary disk 2 and is described in greater detail by referring to FIG'S. 2 and 3. It may be desirable to provide the lenses in disks 3, 4, 5 and 6 with anti-reflective coatings to reduce any internal reflections caused by glare tester 13, particularly if the lenses are located in a refractor between glare tester 13 and eye 9.

Figure 2:
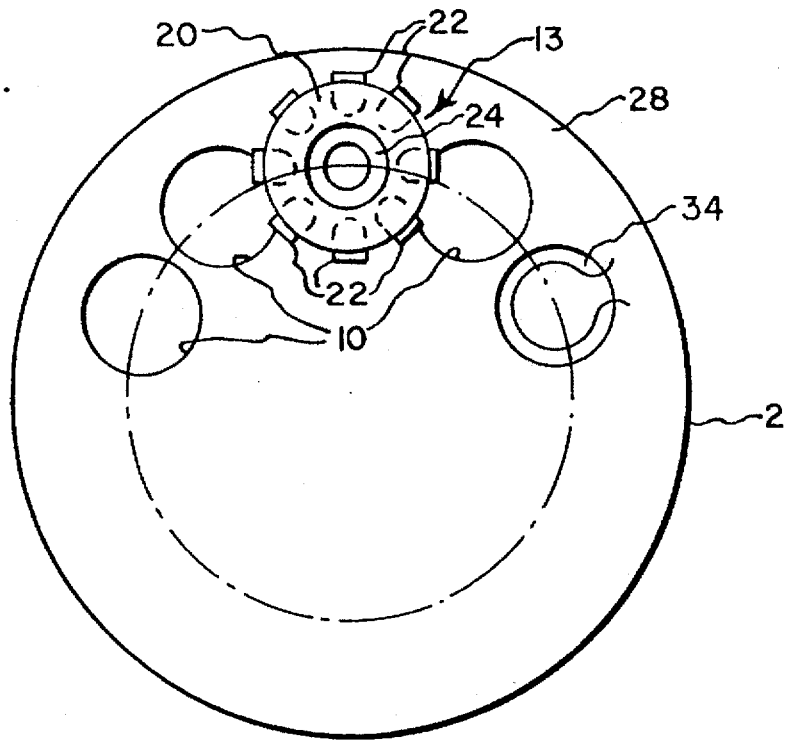
FIG. 2 is a plan view of the preferred embodiment of the glare test option attached to the refractor auxiliary disk.
Figure 3:
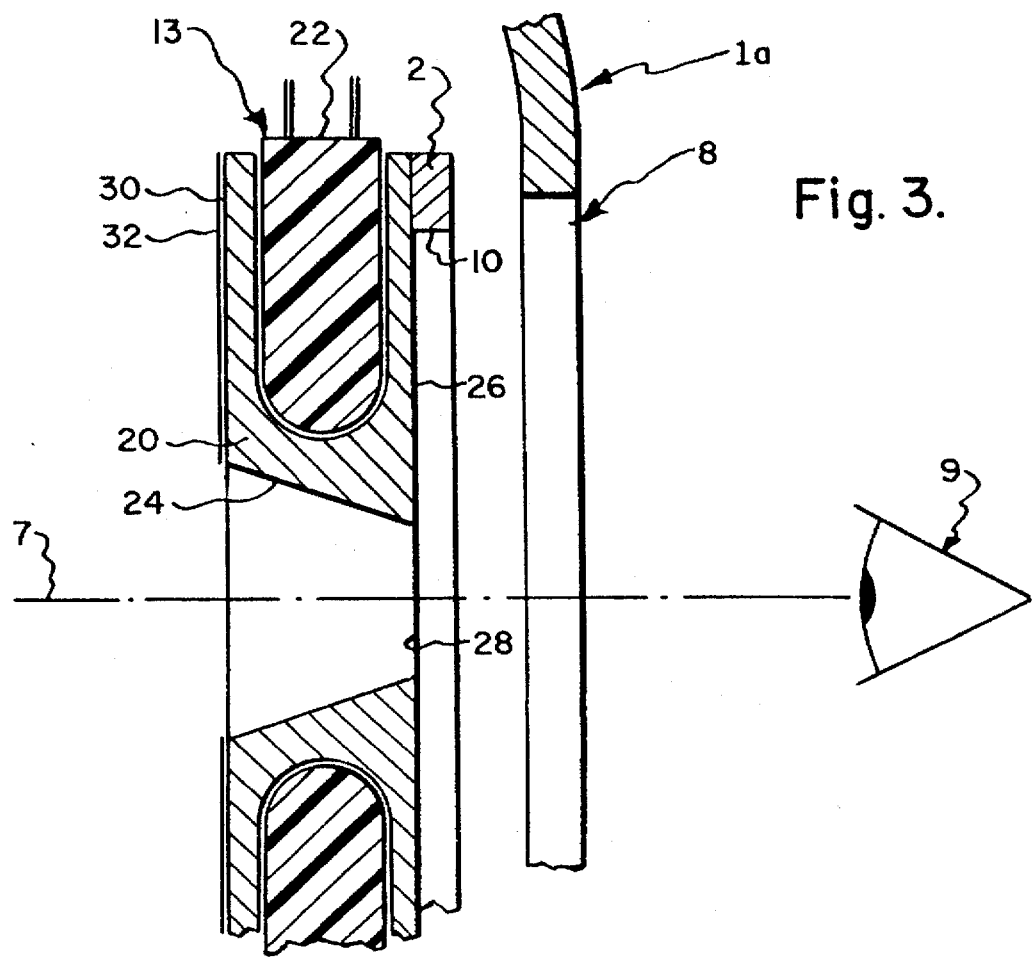
FIG. 3 is an enlargement of portion "A", of the auxiliary disk and glare test option in the refractor battery illustrated in FIG. 1.

In FIG. 2, glare tester 13 is mounted on disk 2 with annular ring 20 being centered with the center of aperture 10. While any translucent material is acceptable for annular ring 20, I prefer to use a translucent plastic. When aperture 10 is located on test axis 7, the center of aperture ring 20 is also centered on test axis 7. A plurality of LEDs 22 are located on spaced radii extending from the center of beveled surface 24 and, when activated, direct visible light toward beveled surface 24 that redirects light from LEDs 22 toward eye 9. Although LEDs 22 may be mounted in recesses or have an end abutted against the periphery of annular ring 20, I believe that embedding the LEDs in plastic during casting of ring 20 is preferable. Referring now to FIG. 3, surface 26 of annular ring 20 is attached to the surface 28 of disk 2 with its center aligned with that of aperture 10 and test axis 7. LEDs 22 are cast into ring 20 and reflective layer 32 is applied or laminated to surface 30, which is on the side opposite eye 9. Silver, nickel and aluminum are examples of acceptable reflective layers. Such reflective layers may be applied to ring 20, for example, by vapor or chemical deposition as well as by adhering a film of such materials to provide an increase in available light from LEDs 22 that is directed toward eye 9.

While only one refractor battery and glare tester has been described, those skilled in the art will recognize that each battery of a conventional refractor should be fitted with an individual testing unit.

Figure 4:
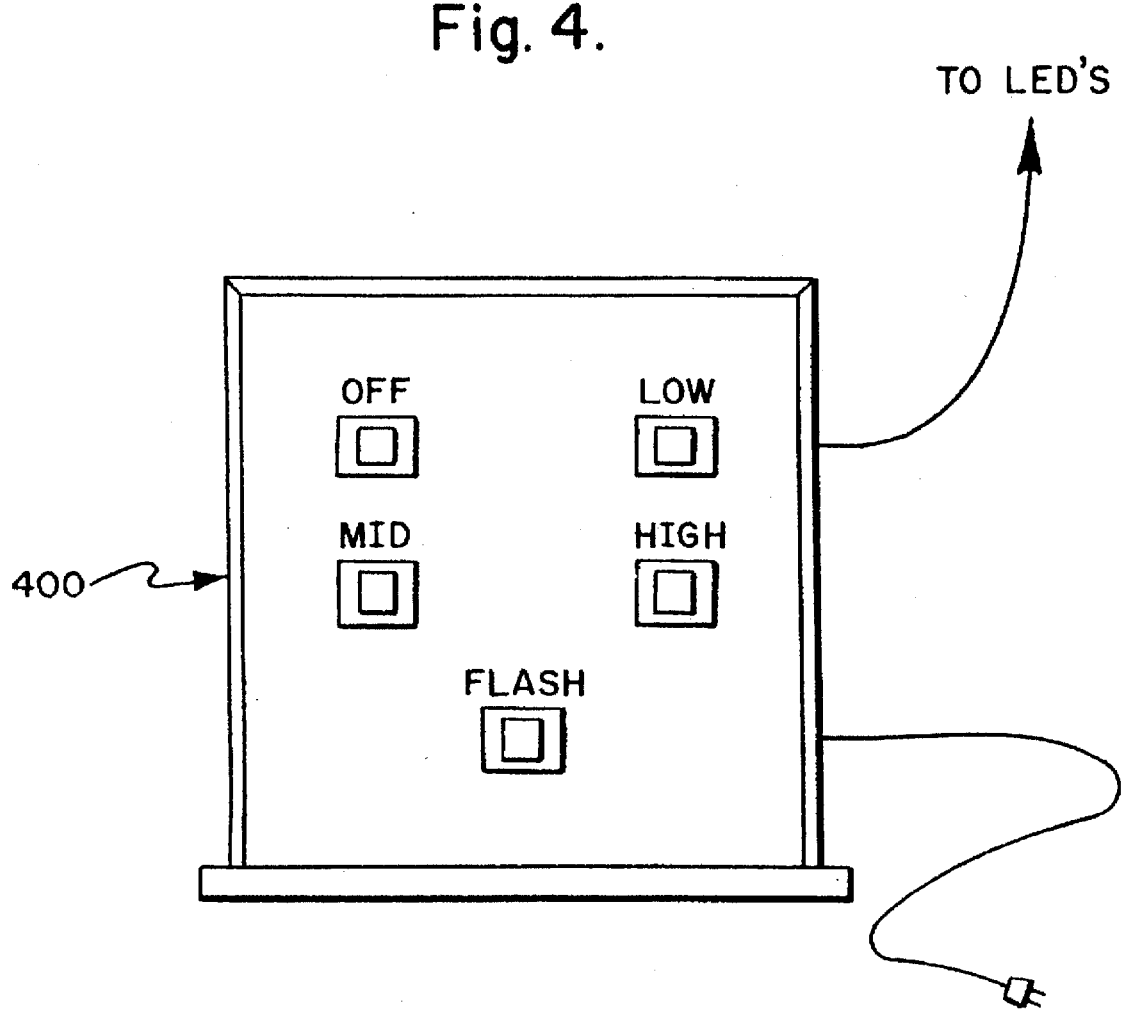
FIG. 4 is a block diagram of a control unit for a glare tester according to the present invention.

The acuity glare test is normally conducted following a conventional acuity test. To conduct the glare test, the doctor rotates auxiliary disk 2 until glare tester 13 is positioned on test axis 7. The amount and type of glare illumination is preferably controlled remotely by a unit of the type illustrated in FIG. 4. Normally the doctor will turn on the LEDs at the low level by pressing the "low" button of control 400 and record any observed change in the patient's acuity. If a substantial impairment is not observed, the illumination is progressively increased by pushing the "mid" button, and if necessary, the "high" button on control 400 and recording observed changes. After the test, the LEDs are turned off by pushing the "off" button.

An additional test for pathology such as cystoid macula edema or central serous maculopathy may be conducted by pressing the flash button on control 400, to briefly flash the LEDs, or an additional light source as shown in FIG. 2 such as a ring xenon flash 34 at a very high level of illumination. Results of this glare test are obtained by determining the time required for the patient's eye to identify a symbol presented on the test chart. Preferably, the operator manually changes the test chart symbol at the same time the flash button is pressed. Those skilled in the art will recognize that any remotely controllable chart projector can be connected to control 400 to automatically change the test symbol upon activation of the flash button. Equally obvious to those skilled in the art is that both glare testers may be simultaneously flashed to determine the combined response time as well as the individual response time for each individual eye.

What I claim is:

1. A refractor for glare testing an eye comprising, a refractor body, a testing axis passing through said eye and body a wheel located in said body and adapted for rotation therein, an aperture positioned in said wheel and selectively positionable on said testing axis, means for subjecting said eye to glare by inundating said eye with visible illumination when said aperture is positioned on said axis, whereby the acuity of said eye may be tested with and without glare or the time for recovery of acuity after glare can be determined.

2. The refractor according to claim 1, wherein said means includes a translucent disk surrounding said aperture.

3. The refractor according to claim 2, wherein said disk has a reflective surface directing visible illumination from said means toward the eye.

4. The refractor according to claim 2, wherein said means has a plurality of sources of visible illumination, said disk is plastic and said plurality of sources are mounted in said disk.

5. The refractor according to claim 4, wherein said disk has a reflective surface directing visible illumination from said plurality of sources toward the eye.

6. The refractor according to claim 5, wherein said sources are LEDs molded into said disk.

7. The refractor according to claim 4, wherein said plurality of sources are LEDs.

8. The refractor according to claim 1, wherein said means includes a plurality of sources of visible illumination spaced around said aperture.

9. The refractor according to claim 1, wherein said means for subjecting the eye to glare includes a control means for varying the illumination intensity.

10. The refractor according to claim 9, wherein a plurality of predetermined levels of intensity are provided by said control means.

11. The refractor according to claim 10, wherein said plurality of predetermined levels of intensity may be adjusted.

12. The refractor according to claim 10, wherein said plurality of predetermined levels of intensity are adjusted by the ambient light level.

13. The refractor according to claim 9, wherein said control means provides an infinitely variable illumination level.

14. The refractor according to claim 1, wherein said means for inundating the eye includes a ring xenon flash.

15. A refractor for testing an eye having a visual axis comprising, means for positioning a selected one of a plurality of corrective lenses on said visual axis and means for selectively subjecting said eye to glare by visible illumination along said visual axis, whereby the acuity of said eye may be tested with and without glare.

16. The refractor according to claim 15, further including a light source and a translucent disk having an aperture for directing light from said source toward the eye.

17. The refractor according to claim 16, wherein said source includes a plurality of LEDs, said disk is plastic and said LEDs are mounted in said disk.

18. A refractor for testing visual acuity along a test axis comprising, a plurality of wheels rotatable about a rotation axis, each of said plurality of wheels having a plurality of apertures selectively positionable on said test axis, one of said wheels having a plurality of corrective lenses mounted thereon for positioning a selected lens and aperture on said test axis, one of said wheels having means for selectively subjecting said eye to glare by visible illumination along said test axis, whereby the acuity of said eye may be tested with and without glare.

19. An accessory for a refractor having an auxiliary wheel containing an opening adapted to be selectively placed on a test axis of said refractor which comprises: an annular plastic ring having a pair of opposed planar surfaces, each of said pair having an inner and an outer diameter, one of said pair having an inner diameter greater than the inner diameter of the other of said pair, a peripheral surface, a plurality of recesses spaced around said peripheral surface, a plurality of LEDs, each of said plurality of LEDs being mounted in a respective one of said plurality of recesses, means to selectively activate said LEDs, and mounting means for holding said one of said pair of surfaces against said wheel axially aligned with said opening.

20. The accessory according to claim 19, further including a reflective coating on said other of said pair of surfaces.

* * * * *